United States Patent
Wu

(10) Patent No.: US 9,902,929 B2
(45) Date of Patent: Feb. 27, 2018

(54) BIOREACTOR FOR THREE-DIMENSIONAL TISSUE PERFUSION CULTURE

(71) Applicant: THE THIRD AFFILIATED HOSPITAL OF THIRD MILITARY MEDICAL UNIVERSITY, Chongqing (CN)

(72) Inventor: Jinjin Wu, Chongqing (CN)

(*) Notice: Subject to any disclaimer, the term of this patent is extended or adjusted under 35 U.S.C. 154(b) by 0 days.

(21) Appl. No.: 15/328,460

(22) PCT Filed: May 20, 2015

(86) PCT No.: PCT/CN2015/079330
§ 371 (c)(1),
(2) Date: Jan. 23, 2017

(87) PCT Pub. No.: WO2015/176653
PCT Pub. Date: Nov. 26, 2015

(65) Prior Publication Data
US 2017/0226462 A1    Aug. 10, 2017

(30) Foreign Application Priority Data

May 22, 2014  (CN) .......................... 2014 1 0218150
May 22, 2014  (CN) ..................... 2014 2 0264095 U

(51) Int. Cl.
*C12M 1/00*    (2006.01)
*C12M 3/00*    (2006.01)
*C12M 1/34*    (2006.01)

(52) U.S. Cl.
CPC ............ *C12M 29/10* (2013.01); *C12M 21/08* (2013.01); *C12M 23/34* (2013.01); *C12M 23/38* (2013.01); *C12M 29/18* (2013.01); *C12M 41/44* (2013.01)

(58) Field of Classification Search
CPC ...... C12M 29/10; C12M 23/34; C12M 21/08; C12M 23/38; C12M 29/18; C12M 41/44
See application file for complete search history.

(56) References Cited

FOREIGN PATENT DOCUMENTS

| CN | 1560225 A    | 1/2005 |
| CN | 103966095 A  | 8/2014 |
| CN | 203855588 U  | 10/2014 |

OTHER PUBLICATIONS

Wang, Yang et al., 'Design and Preliminary Simulation of a New Perfusion Bioreactor for Tissue-Engineered Skin Based on Quasi-Static Plane Flow Field', Acta Academiae Medicinae Militaris Tertiae, vol. 35, No. 7, Apr. 15, 2013 (Mar. 15, 2013), pp. 622-626, particularly p. 623, section 1.1 and figure 1.

*Primary Examiner* — Gautam Prakash
(74) *Attorney, Agent, or Firm* — Novoclaims Patent Services LLC; Mei Lin Wong

(57) ABSTRACT

A bioreactor suitable for perfusion culture of three-dimensional tissues and cells which includes a reaction chamber, a reservoir and a peristaltic pump connected in turn via infusion tubes, wherein the reaction chamber comprises a cover body and a box body including side walls, a bottom wall, a cut-off device, an overflow plate, a screen frame, a static pressure tank, a drainage chute and a drainage trench. The cut-off device is a floodgate or a weir dam. An overflow port which cooperates with the drainage trench is provided, and the screen frame is fixed to two side walls of the box body. The invention can solve the problem of cell death easily caused by non-uniformity of the flow field and uneven transfer of nutrient in the existing perfusion culture, is suitable for three-dimensional culture of tissues and cells, and can improve quality of tissue engineering products.

14 Claims, 5 Drawing Sheets

BIOREACTOR FOR THREE-DIMENSIONAL TISSUE PERFUSION CULTURE

FIELD OF THE PRESENT INVENTION

The present invention belongs to the field of cell culture device, and relates to a bioreactor suitable for perfusion culture of three-dimensional tissues and cells, particularly a bioreactor for co-culture of multiple tissues and organs.

DESCRIPTION OF PRIOR ART

Usually, engineered tissues (or 3D constructs) which have been constructed need to be cultured in vitro for a period of time such that they can be used for transplantation or research after maturity. The static culture method that uses a culture plate to replace fluid regularly is employed most commonly at present. In that method, firstly the old culture medium is removed, and the new culture medium is added and put in the culture case for a static culture. It is the advantage that it is suitable for small batch culture and corresponding strategies can be taken because of the different periods of replacing fluid depending on different tissues and cells. But it has the obvious disadvantages following. Firstly, the consumption of nutrient solution is decreased progressively and metabolic products are increased, which cause some physical damage to cells. Secondly, nutrition is provided by diffusion approach, limiting nutrient supply and even leading to death of cells inside engineered tissue caused by the lack of nutrient. Thirdly, the fluid is replaced regularly such that nutrient fluctuates cyclically, which is unfavourable for the uniform growth of cells.

In vivo, there is a rich capillary network to construct an efficient mass transfer channel, providing adequate oxygen and nutrients for cells. In order to ensure the provision of nutrient in vitro culture, it is necessary to establish an effective fluid circulation method. There are the following strategies: roller bottle culture, rotation culture and perfusion culture. The perfusion culture has significant advantages over the other culture methods. On the one hand, the culture medium can flow continuously inside and around 3D constructed tissues to overcome the disadvantage of limiting the nutrient transmission, therefore, a reliable provision of nutrition can be obtained even if the constructed tissues have a thickness of more than 500 µm. On the other hand, the fluid flow in the perfusion culture can generate a certain shear stress to provide an appropriate mechanical stimulation, facilitating the development and maturation of constructed tissues. Kalyanaraman et al (Kalyanaraman B M, Dorothy M S, Steven T B. Medium Flow Rate Regulates Viability and Barrier Function of Engineered Skin Substitutes in Perfusion Culture. Tis Eng: Part A. 2008, 14(5):583-93) have designed a bioreactive chamber, whose inlet pipe and outlet pipe are respectively connected to a culture chamber at both sides of its bottom, and the height of fluid level in the culture chamber is controlled by setting the height of the outlet pipe, namely, the fluid will flow into the outlet pipe to be discharged when the fluid level in the culture chamber is higher than the outlet pipe. The maturation culture of constructed tissue engineered skin has been performed. The results showed that at the perfusion rate of 5 ml/min or 15 ml/min, the histological structure was better than that under static culture. The cell viability assays showed that the cell viability at the perfusion rate of 5 ml/min was significantly better than that under static culture. The proliferation assay with BrdU incorporation method also showed that the cell proliferation at the perfusion rate of 5 ml/min or 15 ml/min was obviously better than that under static culture. The comparison also found that there were only a small number of cell proliferations at the infusion rate of 50 ml/min. These experimental results proved that low velocity could increase the cell viability and maintain the epidermal barrier, which is suitable for transplantation, while the high shear stress caused by the high velocity might lead to degenerative necrosis of cells.

Although the perfusion culture device at present achieves a simple fluid circulation, but those designs do not take into account the overall situation of the flow field. On the one hand, the culture medium flows instably in the circulation process, changes frequently, and cannot guarantee a low flowrate and uniform flow flied when flowing across tissue engineering products to be cultured, which is unfavorable for cell proliferation. On the other hand, the medium at the edge is not easy to flow, there is a non-uniform flow field and uneven nutrient transfer in the culture device, resulting easily in the uneven cell growth. Moreover, in the case of uneven flowrate the fluid shear stresses applied to the cells have different sizes, the cells are vulnerable to injury because of too large shear stresses at high flowrate, and it is unfavorable for cell proliferation at too low flowrate (near stationary). "A new device design and preliminary simulation of perfusion type biological reactive chamber based on the quasi-static planar flow field for tissue engineering skin" presented on Journal of the Third Military Medical University at Vol. 35 No. 7 by the inventor of the present invention, discloses a perfusion bioreactor comprising a culture bottle, a peristaltic pump, a sterile silicon tube, a buffer tank, an overflow dam, a culture chamber and a drainage ditch. In the bioreactor, a quasi-static planar flow field is generated by the medium in the overflow mode. The medium enters the buffer tank through a high overflow dam into the culture chamber, thus transferring nutrient to tissues and cells in the course of the culture, overflowing from a low overflow dam into the drainage ditch and lastly entering the buffer tank in next layer of the reactor. In the bioreactor, because of the surface tension in the culture medium, the instable pressure head caused by the un-constant and non-uniform flowrate of the culture medium flowing into the buffer tank, and impossibility of absolute smoothness of the drainage slope of the high overflow dam, one or several strands of uneven fluid flow will be formed when the culture medium flows through the high overflow dam after having cumulated potential energy in the buffer tank. Moreover, at low flowrate, a flow cutoff is caused in some regions of the drainage slope, such that the culture medium generates an uneven flow field when entering the cultivation section of the flow field, resulting in injuries and deaths of cells in certain regions due to no or insufficient provision of nutrient and no timely exclusion of their metabolites. Moreover, the existing screens are mostly fixed to a bottom wall of the reactive chamber and need to be fixed by some supports, resulting in that a non-uniform flow field along the flow direction is formed behind fixed pillars of the screen frame, and the effect of culture is adversely affected.

Thus, in perfusion culture, it is very important for the improved quality of tissue engineering products, the reduced breeding time and the increased culture efficiency to make the fluid flowing through tissue cells which will be cultured in an uniform flow field, and to maintain always the fluid at low flowrate.

SUMMARY OF THE PRESENT INVENTION

In view of the problems above, it is an object of the present invention to provide a bioreactor suitable for culture of three dimensional tissues and cells, the bioreactor can achieve an appropriate flowrate of the culture medium in the planar flow field and maintain the flow field uniform and stable. The present invention also provides a stacked bioreactor with a compact structure, good expansibility and more optimized performance.

In order to solve the technical problems described above, a bioreactor suitable for culture of 3D tissues and cells comprises a reservoir, a peristaltic pump and at least one reactive chamber which includes an open-top rectangular box body and a cover body. A cut-off device is fixed to one end of the box body, forming a static pressure tank with the box body, while an overflow plate is fixed to the other end of the box body, constituting a drainage chute with the box body. Between the static pressure tank and the drainage chute, is fixed a screen frame without any contact with the cut-off device and the overflow plate. The screen frame in which a screen is secured, is fixed in the box body. A reactive area is formed between the cut-off device and the overflow plate. In the reactive chamber, is provided an inlet hole which communicates with the static pressure tank and introduces directly fluid into the static pressure tank, and in a wall of the box body, is provided an outlet hole which communicates with the drainage chute and discharges directly fluid from the drainage chute. The cut-off device is provided with a plurality of uniformly arranged permeable holes in the same plane along its longitudinal cross-section, which can introduce evenly fluid within the static pressure tank into the reactive area. An overflow port is provided in a side wall of the static pressure tank, and in a side wall of the box body, is provided a drainage trench which can discharge excess fluid overflowing from the static pressure tank through the overflow port into the drainage chute via an inlet port. The cut-off device is no higher than the box body, the screen frame is lower than cut-off device, and the overflow plate is no lower than the screen on the screen frame. A lower edge of the overflow port is lower than a top surface of the cut-off device but is higher than a top surface of the overflow plate, separate upper border of the inlet port and the permeable hole, in order to form separate fluid levels at different heights in the static pressure tank, the reactive area and the drainage chute, constituting a stepped shape. The reservoir and the peristaltic pump are connected in turn between the outlet hole and the inlet hole by the infusion tubes.

In the present invention, the screen frame is secured to the two side walls of the box body, and the cut-off device, the overflow plate and the screen frame are respectively connected to the box body by engaging connection. Stepped protrusions are provided on surfaces of the cut-off device and the overflow plate which contact with the box body, and in the side walls and a bottom wall of the box body, are provided grooves which engage with the protrusions. It is convenient for the reactive chamber to be dissembled and cleaned by the engaging connection. Comparing to the previous screen frame fixed to the bottom wall, the screen frame being fixed to the side walls of the box body may decrease the screen frame's block of the culture medium in the reactive area, thereby forming an uniform flow field.

Preferably, the overflow hole in the present invention includes an U-groove and a block piece that is arranged in the static tank aside the U-groove. The block piece can cover the U-groove by its rotation around a positioning shaft and can adjust the height of the fluid level in the static pressure tank by adjusting the height of the lower edge of the U-groove. It is convenient to adjust the height of fluid level in the static pressure tank in order to allow culture medium to pass evenly through the permeable holes of the cut-off device by providing the overflow hole.

The permeable holes in the present invention may be a number of uniformly arranged strip-type, circular, semicircular or profiled holes. It is possible to form an uniform flow path when culture medium enters the reaction area in order to achieve an uniform flow field, by providing the permeable holes uniformly.

In the present invention, on a network surface of the screen, is provided a standard mold with the same height as supports of the screen frame, which may be square, circular, triangular or profiled structure.

In the present invention, preferably, the overflow plate is 0-4 mm higher than the screen in the screen frame. A good contact may be formed between culture medium and constructed tissues on the screen by providing the overflow plate slightly higher than the screen.

In a modified scheme of the present invention, the cut-off device may be a floodgate with the permeable holes which are located in the middle-lower part of the floodgate.

In another modified scheme of the present invention, the cut-off device may be a weir dam with a drainage slope, which comprises an upper dam body and a lower dam body, the drainage slope being arranged on a side of the lower dam body adjacent to the screen frame, and the permeable holes being located in the upper dam body of the weir dam. The drainage slope has an included angle of 15°-25° with a bottom surface of the box body, and has a ⅓-½ height of the weir dam.

Comparing to the existing cut-off devices, the two modified cut-off devices described above not only may achieve an uniform flow field when culture medium passes through the permeable holes, but also may be dissembled and cleaned conveniently.

In another modified scheme of the present invention, is provided a stacked box body which can be produced in batch, and may be formed by engaging reversely the box bodies with each other.

In the present invention, the box body of the bioreactor is provided with stepped flanges outside upper surfaces at its side walls, and recesses around its bottom wall, which engages with the flange in the upper surface of the side wall. Multiple box bodies are reversely engaged with each other to form a stacked box body, and the box body on the top is covered by the cover body, the cover body forming a reactive chamber with the top box body, and a bottom of an upper box body forming a reactive chamber with an adjacent lower box body. An outlet hole of an upper box body and an inlet hole of an adjacent lower box body in the stacked box body are connected via an infusion pipe, and the outlet hole of the bottom box body of the stacked box body is connected with the inlet hole of the top box body via the infusion pipe, the reservoir and the peristaltic pump. The stacked box body, together with the cover body, the infusion pipe, the reservoir and the peristaltic pump, is formed into a stacked bioreactor.

In the preferred modified schemes described above, an outlet hole of an upper box body in the stacked box body is provided in a bottom wall of its drainage chute, communicates with a static pressure tank of an adjacent lower box body, and constitutes an inlet hole of the lower box body in order to allow fluid flow directly from the upper box body of the stacked box body into the static pressure tank of the lower box body. The structure of the stacked bioreactor is simplified by providing an outlet hole in a bottom wall.

Preferably, the stacked box body may have 2-20 box bodies. In the stacked bioreactor described above, outside the stacked box body, is provided a sterile reactive case which is composed of a case body and a case cover and is provided with channels. The channels through which the infusion tubes can pass, cooperate with the inlet hole of the top box body and the outlet hole of the bottom box body of the stacked box body. The stacked box body is located inside the case body and the reservoir and the peristaltic pump are located outside the case body. The stacked bioreactor can achieve a sterile and closed reaction environment.

Around the periphery of the reactive case, is also arranged a circulating water jacket, outside which the reservoir and the peristaltic pump are positioned, thereby maintaining a constant temperature inside the bioreactor.

In the above technical schemes, culture medium cumulates in the static pressure tank when being introduced therein, and the height of the overflow hole is adjust to allow excess fluid overflow from it, ensuring that fluid can flow slowly into the bottom of the screen frame through the permeable holes in the cut-off device after a stable pressure is formed in the static pressure tank. Moreover, without the block of supports of the screen frame in the flow field, a stable and uniform planar flow field is formed in the middle of the reactive box body, achieving an uniform diffusion of nutrient. Because culture medium flows naturally into the bottom of the screen frame after a stable pressure is formed inside the static pressure tank, the culture medium flowing into the bottom of the screen frame is always kept at a low, even and stable flowrate, which can provide uniform shear stresses for three dimensional tissues and organs or tissue engineering products on the screen frame to be cultured or produced, facilitating cell proliferation and tissue development.

The present invention provides a bioreactor suitable for perfusion culture of three-dimensional tissues and organs, cells or tissue engineering products, particularly for perfusion culture (including co-culture) of tissue engineering skins or other membrane-like tissues such as cornea, heart valves, various tissues and organs and cells. It works on the principle following. Firstly, a raw material solution of three-dimensional constructed tissues to be researched or tissue engineering products to be produced, is poured into the screen frame, and is formed into a specific shape with standard specification by putting the standard mold on the screen, and then the mold is removed and the box body is covered by the cover body. Subsequently, culture medium is poured into the static pressure tank, and cumulates in the static pressure tank, and excess fluid overflows from the overflow port, ensuring that fluid flows into the screen frame through the permeable holes in the cut-off device after a stable pressure is formed inside the static pressure tank, such that an uniform and stable planar flow field is formed in the middle of the reactive box body, and the three dimensional tissues and organs or tissue engineering products on the screen frame are just submerged by the flowing nutrient fluid. It is also possible to maintain three dimensional tissues on the screen frame to be cultured always in a culture state of gas-fluid interface by decreasing the height of fluid level, in order to provide sufficient nutrient and appropriate shear stress for the three dimensional tissues and organs or tissue engineering products to be researched or produced. When the fluid level in the middle of the box body is higher than the overflow plate, the culture medium flows into the drainage chute across the top of the overflow plate, enters into the reservoir from the outlet hole, and is again pumped into the static pressure tank by the peristaltic pump, achieving a closed cyclic culture.

The present invention has the following advantages by the above structures.

1. By providing the overflow port and the cut-off device with the permeable holes, the permeable holes introducing evenly fluid in the static pressure tank at a constant speed into the reactive area, the culture medium can easily act against surface tension to form an uniform flow path when passing through the permeable holes, such that the culture medium is always kept at a relatively low, stable and uniform flowrate when flowing through the screen frame, and a stable and uniform planar flow field is formed in the reactive area of the reactive box body, facilitating cell proliferation.
2. The bioreactor of the present invention may be employed separately, may also be used in series or in stack, and has a good extensibility, not only maintaining biological characteristics of 3D tissues and organs and ensuring quality of 3D tissues and organs or products, but also improving efficiency of a basic research and production.
3. In the present invention, the cut-off device, the standard mold, the screen frame and the overflow plate can be dissembled and replaced as desired, which is not only suitable for culture of tissue engineering skin and film-like materials such as cornea, heart valves, nerves, blood vessels, mesentery or other tissues and organs, but also suitable for co-culture of different types of tissues and organs at the same time. The bioreactor can also be used to culture seed cells on adherent growth after the screen frame is dissembled, and has the characteristics of a strong versatility and wide applicability.

A LIST OF REFERENCE NUMERALS

Figure 1:
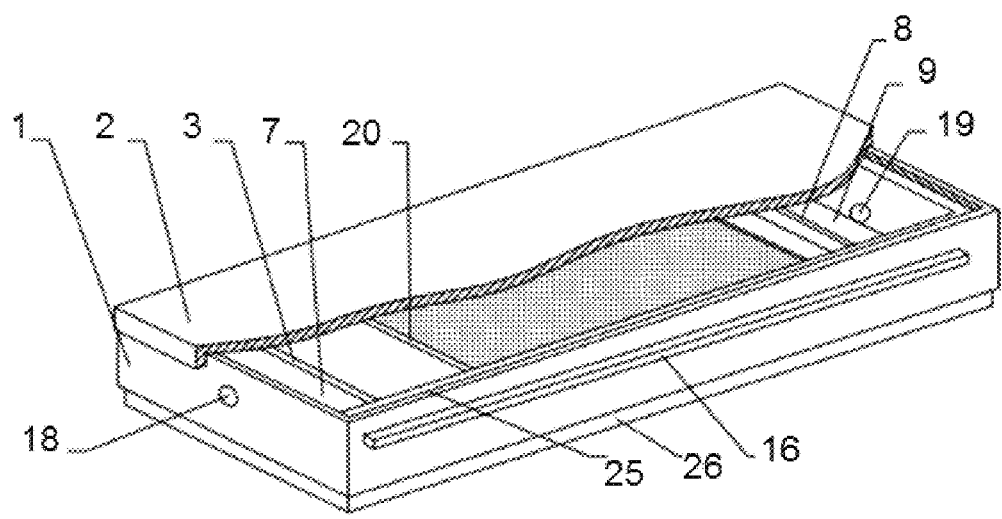
FIG. 1 is a three-dimensional diagram of a reactive chamber according to the present invention.

1: box body
2: cover body
3: cut-off device
4: floodgate
5: weir dam
6: permeable hole
7: static pressure tank
8: overflow plate
9: drainage chute
10: upper dam body
11: lower dam body
12: drainage slope
13: overflow port
14: positioning shaft
15: block piece 16: drainage trench
17: inlet port
18: inlet hole
19: outlet hole
20: screen frame
21: screen
22: standard mold
23: protrusion
24: groove
25: flange
26: recess
27: infusion tube
28: reservoir
29: peristaltic pump
30: stacked box body
31: case body
32: case cover
33: circulating water jacket
34: channel

DETAILED DESCRIPTION OF THE PRESENT INVENTION

The following detailed description of the present invention will be given in combination with the accompany drawings.

The First Embodiment

Referring now to FIGS. 1, 2, 3, 4, 6 and 9, a bioreactor of the present invention suitable for three dimensional perfusion culture of tissues and cells includes a reservoir 28, a peristaltic pump 29, and at least one reactive chamber which comprises an open-top rectangular box body 1 and a cover body 2. A cut-off device 3 is fixed to one end of the box body 1, forming a static pressure tank 7 with the box body 1, while an overflow plate 8 is fixed to the other end of the box body 1, constituting a drainage chute 9 with the box body 1. Between the static pressure tank 7 and the drainage chute 9, is fixed a screen frame 20 without any contact with the cut-off device 3 and the overflow plate 8. The screen frame 20 in which a screen 21 is secured, is engaged fixedly in the two side walls of the box body 1. The cut-off device 3 is provided with a plurality of uniformly arranged permeable holes 6 in the same plane along its longitudinal cross-section, which can introduce fluid within the static pressure tank 7 evenly into a reactive area at a constant rate, and may be a number of uniformly arranged strip-type, circular, semicircular or other profiled holes. In a side wall common to the static pressure tank 7 and the box body 1, is provided an overflow port 13 which comprises an U-groove and a block piece 15 that is arranged in the static tank 7, and the block piece 15 can cover the U-groove and adjust the height and the size of the U-groove by its rotation about a positioning shaft 14. In the side wall of the box body 1, is provided a drainage trench 16 which can discharge excess fluid overflowing from the static pressure tank 7 through the overflow port 13 into the drainage chute 9 via an inlet port 17. In the reactive chamber, is provided an inlet hole 18 which is in communication with the static pressure tank 7 and can introduce directly fluid into the static pressure tank 7. In a wall of the box body 1, is provided an outlet hole 19 which is in communication with the drainage chute 9 and can discharge directly fluid from the drainage chute 9. The cut-off device 3 is no higher than the box body 1, the screen frame 20 is lower than the cut-off device 3, and the overflow plate 8 is no lower than the screen 21 on the screen frame 20. A lower edge of the overflow port 13 is lower than a top surface of the cut-off device 3 but is higher than a top surface of the overflow plate 8, upper edges of the inlet port 17 and the permeable holes 6. The reservoir 28 and the peristaltic pump 29 are connected in turn between the outlet hole 19 and the inlet hole 18 by an infusion tube 27.

Figure 2:
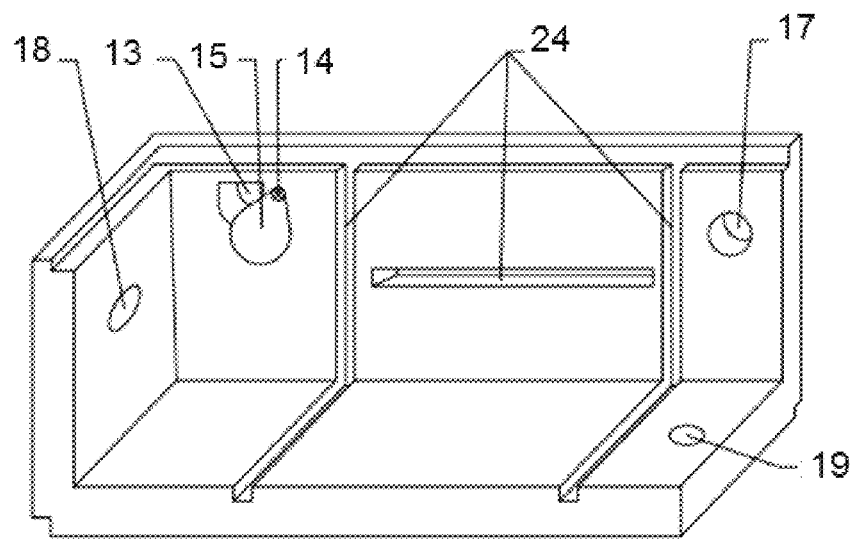
FIG. 2 is a three-dimensional diagram of a body wall of a box body according to the present invention.
Figure 3:
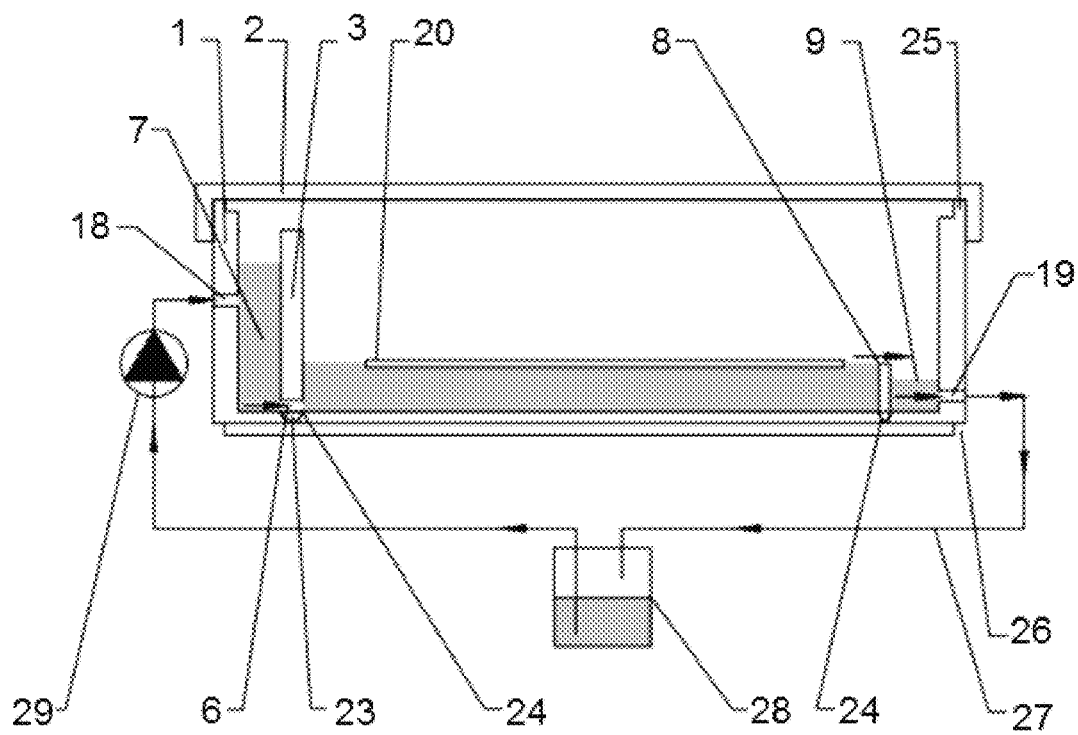
FIG. 3 is a structural schematic diagram of a bioreactor according to the present invention.
Figure 4:
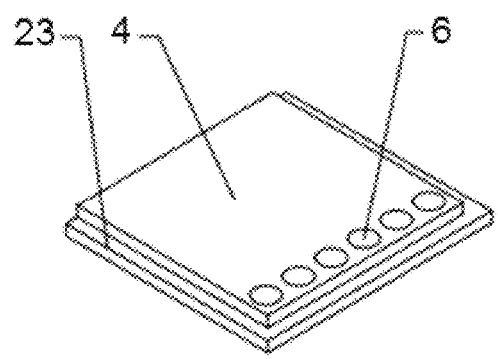
FIG. 4 is a three-dimensional diagram of a floodgate according to the present invention.
Figure 5:
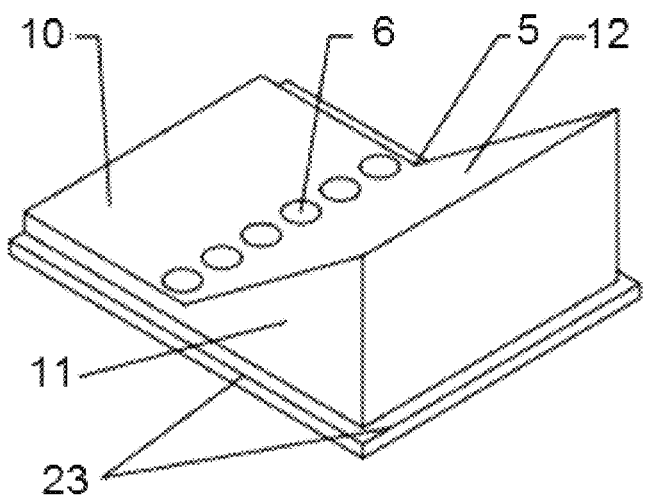
FIG. 5 is a three-dimensional diagram of a weir dam according to the present invention.
Figure 6:
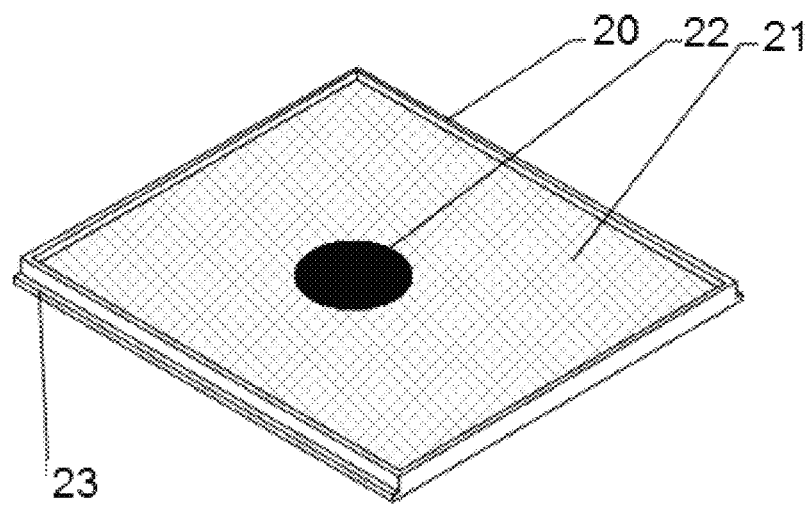
FIG. 6 is a three-dimensional diagram of a screen and a screen frame according to the present invention.
Figure 9:
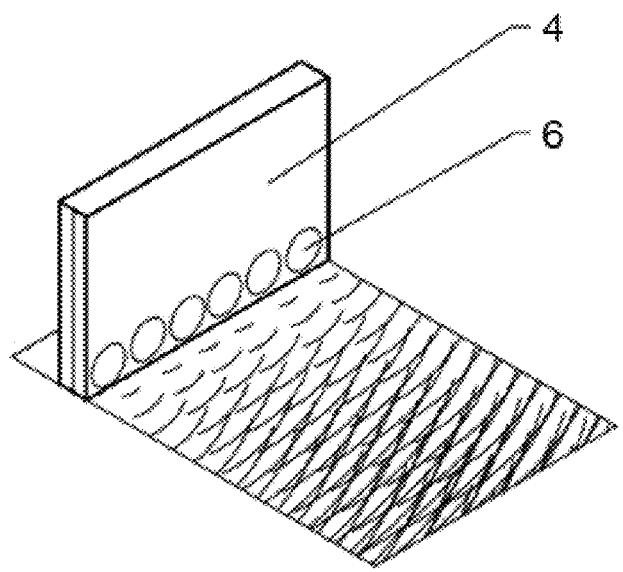
FIG. 9 is a schematic view of a flow field according to the present invention.

As shown in FIGS. 2 and 3, the cut-off device 3 in the embodiment is a floodgate 4. During the peristaltic pump 29 pumps culture medium in the reservoir 28 into the static pressure tank 7, when the culture medium level in the static pressure tank 7 is higher than the permeable holes 6, the excess culture medium overflows from the overflow port 13, and enters into the drainage chute 9 through the drainage trench 16 and the inlet port 17. The culture medium passes through the permeable holes 6 in the floodgate 4 and flows slowly into a bottom of the screen frame 20, such that an uniform planar flow field (as seen in FIG. 9) is generated in a middle part of the box body 1 to make a uniform diffusion of nutrient, and shear stresses are uniformly exerted on tissue engineering products on the screen 21 to be produced, thereby avoiding cell death due to the uneven diffusion of nutrient or the too high shear stresses.

In order to make a wider application and a more convenient disassembly and cleaning in the present invention, engaging grooves 24 are provided in the side walls and the bottom wall of the box body 1, and protrusions 23 which can be inserted into the said engaging recesses 23 to be fastened therein, are provided in the floodgate 4, the screen frame 20 and the overflow plate 8, which can be separately fastened to the box body 1. The overflow plate 8 is 0-4mm higher than the screen 21 on the screen frame 20. The height of fluid level in the middle portion of the box body can be adjusted by replacing the overflow plate 8, thereby not only providing a gas-fluid interface culture environment for tissue engineered skin, but also providing a submerged culture environment for film-like materials such as cornea, heart valves, nerves, blood vessels and mesentery. The size of the shear stresses in the flow field and the height of fluid level can be adjusted by replacing the floodgate 4, the screen frame 20, the overflow plate 8 and the block piece 15, not only for the cultivation of other three dimensional tissues and organs (such as livers, kidneys, lungs, bones and cartilages) and cells (such as stem cells and cancer cells), but also for the cultivation of adherent seed cells when removing the screen frame 20.

The said screen frame 20 may be an integral member, or may be a plurality of separate screen frames arranged at a certain distance. The standard mould 22 is stuck in the screen 21 on the screen frame 20 with the same height as supports of the screen frame 20, and can be designed as a square, circular, triangular or profiled structure, based on the demand of products.

(1) A raw material solution of three-dimensional constructed tissues to be researched or tissue engineering products to be produced, is poured into the screen frame 20, and is formed into a specific shape with standard specification by putting the standard mold 22 on the screen 21, and then the mold 22 is removed and the box body 1 is covered by the cover body 2. Subsequently, the culture medium is poured into the static pressure tank 7 at a high rate of 400 ml/min. When the fluid level of the culture medium rises to a certain height, the block piece 15 of the overflow port 13 is rotated to adjust the height and size of the overflow port 13, such that a small amount of the culture medium just overflows from the overflow port 13, thereby generating a stable static pressure to allow the culture medium flow from the permeable holes 6 in the floodgate 4 to the screen frame 20. It shows by experimental comparisons that at the low rate of 400 ml/min, the perfusion is performed twice a day and a half hour each time, and the cultivation is performed for 10 days, thereby the cell proliferation being 2.37 times of that under the static culture for the same days, and decreasing the time for cultivation of tissue engineering skin by 5 days.

(2) A raw material solution of three-dimensional constructed tissues to be researched or tissue engineering products to be produced, is poured into the screen frame 20, and is formed into a specific shape with standard specification by putting the standard mold 22 on the screen 21, and then the mold 22 is removed and the box body 1 is covered by the cover body 2. Subsequently, the culture medium is poured into the static pressure tank 7 at a medium rate of 200 ml/min. When the fluid level of the culture medium rises to a certain height, the block piece 15 of the overflow port 13 is rotated to adjust the height and size of the overflow port 13, such that a small amount of the culture medium just overflows from the overflow port 13, thereby generating a stable static pressure to allow the culture medium flow from the permeable holes 6 in the floodgate 4 to the screen frame 20. It shows by experimental comparisons that at the low rate of 200 ml/min, the perfusion is performed twice a day and a half hour each time, and the cultivation is performed for 10 days, thereby the cell proliferation being 2.48 times of that under the static culture for the same days, and decreasing the time for cultivation of tissue engineering skin by 5 days.

(3) A raw material solution of three-dimensional constructed tissues to be researched or tissue engineering products to be produced, is poured into the screen frame 20, and is formed into a specific shape with standard specification by putting the standard mold 22 on the screen 21, and then the mold 22 is removed and the box body 1 is covered by the cover body 2. Subsequently, the culture medium is poured into the static pressure tank 7 at a low rate of 100 ml/min. When the fluid level of the culture medium rises to a certain height, the block piece 15 of the overflow port 13 is rotated to adjust the height and size of the overflow port 13, such that a small amount of the culture medium just overflows from the overflow port 13, thereby generating a stable static pressure to allow the culture medium flow from the permeable holes 6 in the floodgate 4 to the screen frame 20. It shows by experimental comparisons that at the low rate of 100 ml/min, the perfusion is performed twice a day and a half hour each time, and the cultivation is performed for 10 days, thereby the cell proliferation being 2.75 times of that under the static culture for the same days, and decreasing the time for cultivation of tissue engineering skin by 5 days.

As shown in FIGS. 1, 2, 3, 5, 6 and 9, the function of the floodgate 4 in the first embodiment may be also achieved by a weir dam 5 which includes a upper dam body 10 and a lower dam body 11, a drainage slope 12 is provided at a side of the lower dam body 11 adjacent to the screen frame 20, and the permeable holes are located in the upper dam body 10 of the weir dam. The drainage slope 12 has an included angle of 15°-25° with the bottom surface of the box body, and has a ⅓-½ height of the weir dam. In order to prevent the screen frame 20 from suffering greatly impact from the medium flowing across the drainage slope 12 which has a certain height, the height of the drainage slope 12 can be adjusted to maintain the fluid flowing to the screen frame 20 in a state of low flowrate.

The Third Embodiment

Figure 7:
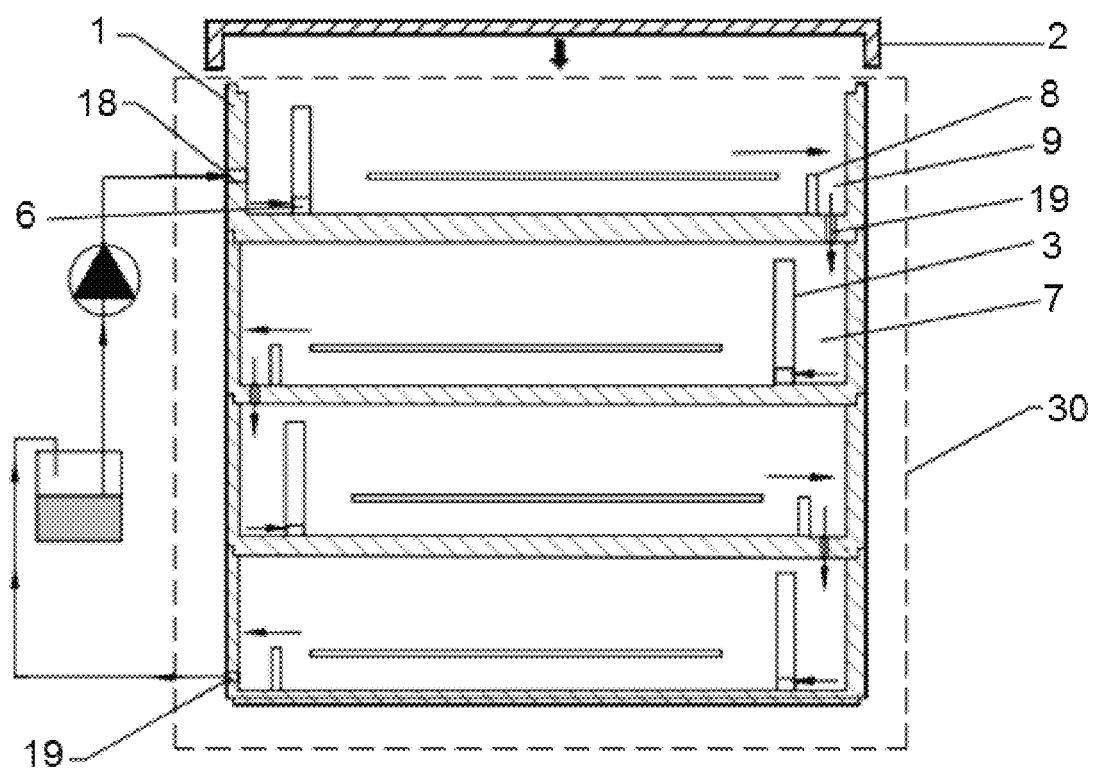
FIG. 7 is a structural diagram of a stacked bioreactor according to the present invention.

Referring to FIGS. 1,3 and 7, in the first or second embodiment, the box body 1 of the bioreactor is provided with stepped flanges 25 outside upper surfaces at its side walls, and is provided with recesses 26 around its bottom wall, which engages with the flanges 25 in the upper surfaces of the side walls. Multiple box bodies 1 are reversely fitted with each other to form a stacked box body 30, the box body 1 on the top is covered by the cover body 2, a bottom wall of an upper box body 1 in the stacked box body 30 forms a reactive chamber with an adjacent lower box body 1, and the top box body 1 forms a reactive chamber with the cover body 2. In a bottom of an upper box body 1, is located an outlet hole 19 which constitutes an inlet hole 18 of an adjacent lower box body 1 and can introduce directly fluid from the drainage chute 9 of the upper box body 1 into the static pressure chute 7 of the adjacent lower box body 1. The inlet hole 18 of the top box body 1 is located in its reactive chamber, and introduces directly the fluid discharged from the outlet hole 19 of the bottom box body 1 into the static pressure tank 7 via the peristaltic pump 29. The stacked box body 30 may have 2-20 box bodies 1, and forms a stacked bioreactor together with the cover body 2, the infusion tubes 27, the reservoir 28 and the peristaltic pump 29.

In use, the culture medium flows from the static pressure tank 7 of the top box body through the cut-off device 3, the screen frame 20 and the overflow plate 8 into the drainage chute 9, the excess fluid overflows from the overflow port 13 through the drainage trench 16 into the drainage chute 9, is then introduced directly into a static pressure tank 7 of an adjacent lower box body 1 via its outlet hole 19, and subsequently flows from the outlet hole 19 of the bottom box body 1 into the reservoir 28. Thereafter, the culture medium in the reservoir 28 is pumped into the static pressure tank 7 of the top box body 1 via the peristaltic pump 29, thereby achieving a closed circulation of the culture medium. The number of the box bodies 1 assembled in the middle portion may be increased or decreased as desired. All the fluid flowing through the middle portions of the box bodies 1 is maintained always in a state of low flowrate due to such a cycle flow, such that tissue engineering products to be produced or three dimensional tissues and organs to be cultivated, on the screen frame 20, may be provided with sufficient nutrient and appropriate shear stresses, thereby ensuring the quality of products.

The box body 1 shown in FIGS. 1 and 3 may also be used as a box body 1 of the stacked box body 30 in the embodiment. In use, an outlet hole 19 of an upper box body 1 and an inlet hole 18 of an adjacent lower box body 1 in the stacked box body 30 may also be connected via an infusion tube 27.

The Fourth Embodiment

Figure 8:
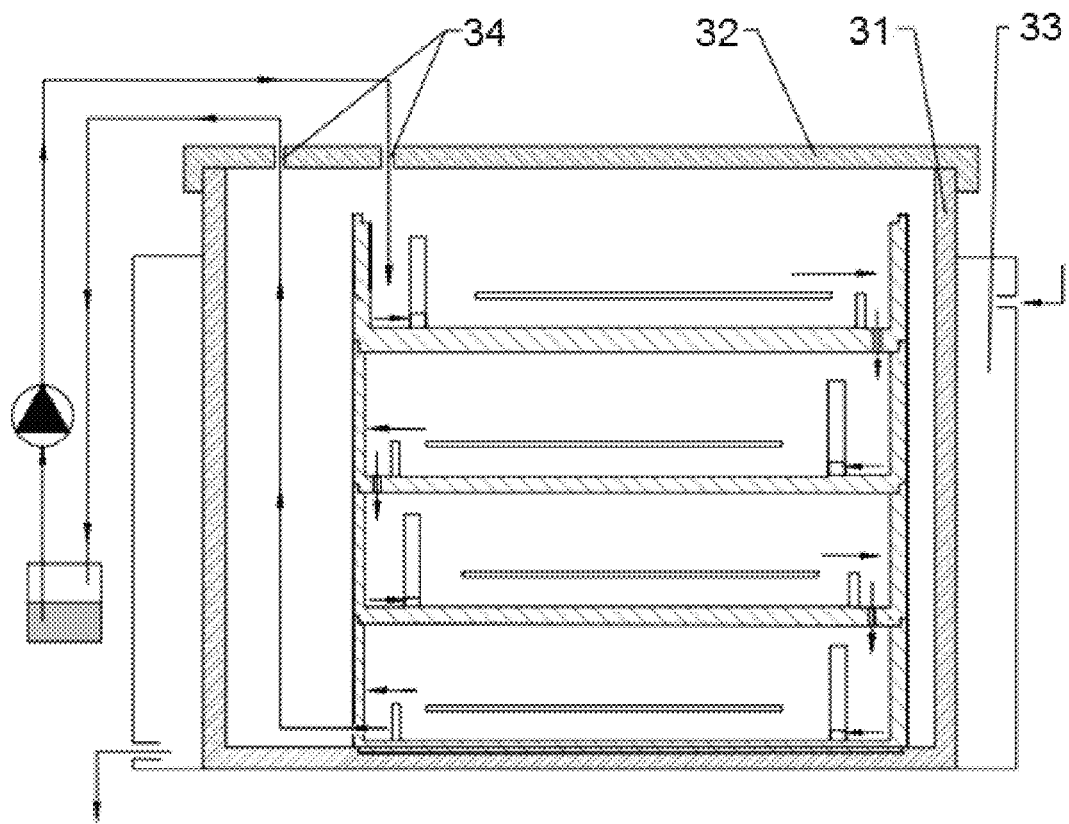
FIG. 8 is a structural diagram according to the third embodiment of the present invention.

In FIG. 8, the stacked box body 30 in the third embodiment is placed in a sterile reactive case which is composed of a case body 31 and a case cover 32 and is provided with channels 34. The channels 34 through which the infusion tubes 27 can pass, cooperate with the inlet hole 18 of the top box body 1 and the outlet hole 19 of the bottom box body 1 of the stacked box body 30. The stacked box body 30 is located inside the case body 31, and the reservoir 28 and the peristaltic pump 29 are located outside the case body 31.

On the periphery of the reactive case, is also arranged a circulating water jacket 33 outside which the reservoir 28 and the peristaltic pump 29 are positioned. In use, the reactive case can maintain the stacked box body 30 in a sterile environment, and the circulating water jacket can maintain the stacked box body 30 at a constant temperature. The culture medium flows circularly inside and outside the reactive case, and all the fluid flowing through the middle portions of the box bodies 1 is maintained always in a state of low flowrate, such that tissue engineering products to be produced or three dimensional tissues and organs to be cultivated, in the reactive case, may be provided with sufficient nutrient and appropriate shear stresses. The circulating water jacket 33 arranged outside the reactive case ensures that a reactive state of constant temperature can be maintained in the reactive case.

In the present invention, regardless of the perfusion rate, the culture medium can generate a stable pressure in the static pressure tank 7, is always kept at a low flowrate when flowing through the screen frame 20, and an uniform and stable planar flow field is generated in the middle portion of the box body 1, by providing the floodgate 4 or the weir dam 5 to cooperate with the overflow port 13. Thereby, the cell necrosis is avoided, which is easily caused by non-uniformity of the flow field and uneven transfer of nutrient in the existing perfusion culture, the quality of products is improved, and the time of cultivation is reduced. It is also applicable for a co-culture research and drug screening of three-dimensional constructs or tissues and organs. The present invention also has the characteristics of a good scalability, strong versatility, wide applicability, realizing the standardization culture of tissue engineering products, greatly reducing the labor intensity, improving the productive efficiency, and having a good popularization and application value.

Obviously, all the embodiments described above are only a part of embodiments of the present invention, rather than all of it. All other embodiments obtained by the skilled one in the art without creative work, based on the embodiments of the present invention, will fall within the scope of the present invention.

What is claimed is:

1. A bioreactor suitable for perfusion culture of three-dimensional tissues and cells comprising: a reservoir (28); a peristaltic pump (29); a cover body (2); and at least one reactive chamber which comprises an open-top rectangular box body (1); the said box body (1), at its one end, being provided with a cut-off device (3) which forms a static pressure tank (7) with the box body (1), and at its other end, being provided with a overflow plate (8) which forms a drainage chute (9) with the box body (1); wherein between the static pressure tank (7) and the drainage chute (9), is provided a screen frame (20) without any contact with the cut-off device (3) and the overflow plate (8);

wherein in the said reactive chamber(s), is provided an inlet hole (18) which is in communication with the static pressure tank (7) and can introduce directly fluid into the static pressure tank (7); in a wall of the box body (1), is provided an outlet hole (19) that is in communication with the drainage chute (9) and can discharge directly fluid from the drainage chute (9);

wherein the said cut-off device (3) is no higher than the box body (1), the screen frame (20) is lower than the cut-off device (3), and the overflow plate (8) is no lower than the screen (21) on the screen frame (20);

wherein the reservoir (28) and the peristaltic pump (29) are connected in turn between the outlet hole (19) and the inlet hole (18) by infusion tubes (27);

characterized in that in a side wall of the said static pressure tank (7), is provided an overflow port (13) which can adjust the height of the fluid level inside the static tank to form a stable static pressure;

that in a side wall of the box body (1), is provided a drainage trench (16), which can discharge excess fluid overflowing the static pressure tank (7) through the overflow port (13) into a drainage chute (9) via an inlet port (17);

that the said cut-off device (3) is provided with a plurality of uniformly arranged permeable holes (6) in the same plane along its longitudinal cross-section, which can introduce fluid within the static pressure tank (7) evenly into a reactive area at a constant rate;

and that the flow rate of fluid in the inlet hole (7), and the height and size of the overflow port (13) are adjusted to form separate fluid levels at different heights in the static pressure tank (7), the reactive area and the drainage chute (9), constituting a stepped shape.

2. The bioreactor suitable for perfusion culture of three-dimensional tissues and cells according to claim 1, characterized in that the screen frame (20) is fixed to the two side walls of the box body (1), that protrusions (23) are provided in the surfaces of the cut-off device (3) and the overflow plate (8) which contact with the box body (1) and in the surfaces of the screen frame (20) which contact with the side walls of the box body (1), and that in the side walls and a bottom wall of the box body (1), are provided engaging grooves (24) which engage with the protrusions (23).

3. The bioreactor suitable for perfusion culture of three-dimensional tissues and cells according to claim 1, characterized in that the said overflow port (13) includes an U-groove and a block piece (15) that is arranged in the static tank (7) aside the U groove, can cover the U-groove by its rotation around a positioning shaft (14) and can adjust the height of the fluid level in the static pressure tank (7) by adjusting the height of a lower edge of the U-groove.

4. The bioreactor suitable for perfusion culture of three-dimensional tissues and cells according to claim 1, characterized in that the said permeable holes (6) are a number of uniformly arranged strip-type, circular, semicircular or other profiled holes.

5. The bioreactor suitable for perfusion culture of three-dimensional tissues and cells according to claim 1, characterized in that the said overflow plate (8) is 0-4mm higher than the screen (21) on the screen frame (20).

6. The bioreactor suitable for perfusion culture of three-dimensional tissues and cells according to claim 1, characterized in that the said cut-off device (3) is a rectangular floodgate (4), and the permeable holes (6) are located in the middle-lower part of the floodgate (4).

7. The bioreactor suitable for perfusion culture of three-dimensional tissues and cells according to claim 1, characterized in that the said cut-off device (3) is a weir dam (5) which comprises a upper dam body (10) and a lower dam body (11), a side of the weir dam (5) facing to the static pressure tank (7) being rectangular, a side of the lower dam body (11) adjacent to the screen frame (20) being a drainage slope (12) whose lower edge is flush with a bottom of the weir dam (5), wherein the said drainage slope (12) has a included angle of 15°-25° with a bottom surface of the box body (1) and has a ⅓-½ height of the weir dam (5), and the said permeable holes (6) are located in the upper dam body (10).

8. The bioreactor suitable for perfusion culture of three-dimensional tissues and cells according to claim 1, characterized in that on the screen (21), is provided a standard mold adhered with cells, which is a square, circular, triangular or profiled structure.

9. The bioreactor suitable for perfusion culture of three-dimensional tissues and cells according to claim 1, characterized in that multiple box bodies (1) are reversely and fixedly stacked with each other to form a stacked box body (30), and the top box body (1) is covered by the cover body (2), the cover body (2) forming a top reactive chamber with the top box body (1);

that in the stacked box body (30), an outlet hole (19) of a box body (1) and an inlet hole (18) of an adjacent lower box body (1) are connected with each other;

and that the reservoir (28) and the peristaltic pump (29) are connected between the outlet hole (19) of the bottom box body (1) and the inlet hole (18) of the top box body (1) of the stacked box body (30) via the infusion tubes (27).

10. The bioreactor suitable for perfusion culture of three-dimensional tissues and cells according to claim 9,
characterized in that the stacked box body may have 2-20 box bodies.

11. The bioreactor suitable for perfusion culture of three-dimensional tissues and cells according to claim 9,
characterized in that the said box bodies (1) are provided with stepped flanges (25) outside upper surfaces at their side walls, and are provided with recesses (26) in their bottom walls, which engage with the flanges (25), the multiple box bodies (1) being reversely fitted with each other by engaging the flanges (25) with the recesses (26) to form the stacked box body (30).

12. The bioreactor suitable for perfusion culture of three-dimensional tissues and cells according to claim 9,
characterized in that the outlet hole (19) in the bottom box body (1) of the said stacked box body (30) is located in its side wall, and outlet holes (19) of the other box bodies (1) are located respectively in their bottom walls and can introduce directly fluid in the corresponding drainage chutes (9) into the corresponding static pressure tanks (7) of the corresponding adjacent lower box bodies (1), respectively.

13. The bioreactor suitable for perfusion culture of three-dimensional tissues and cells according to claim 9,
characterized in that outside the said stacked box body (30), is provided a reactive case which is composed of a case body (31) and a case cover (32), and the reactive case is provided with channels (34) through which the infusion tubes (27) may pass, the reservoir (28) and the peristaltic pump (29) being located outside the reactive case.

14. The bioreactor suitable for perfusion culture of three-dimensional tissues and cells according to claim 9,
characterized in that around the periphery of the reactive case, is also arranged a circulating water jacket (33), outside which the reservoir (28) and the peristaltic pump (29) are positioned.

* * * * *